United States Patent
Barmaimon et al.

(10) Patent No.: US 11,058,605 B2
(45) Date of Patent: Jul. 13, 2021

(54) STERILIZATION FLUID PATH WITH BARRIER REMOVAL

(71) Applicant: FLEX LTD., Singapore (SG)

(72) Inventors: Eyal Barmaimon, Haifa (IL); Lior Shtram, Tel-Aviv (IL); Shai Finkman, Haifa (IL); Christian Riva, Milan (IT); Tommaso Borghi, Milan (IT); David Ward, Milan (IT)

(73) Assignee: FLEX LTD., Singapore (SG)

( * ) Notice: Subject to any disclaimer, the term of this patent is extended or adjusted under 35 U.S.C. 154(b) by 17 days.

(21) Appl. No.: 16/295,818

(22) Filed: Mar. 7, 2019

(65) Prior Publication Data
US 2019/0274924 A1    Sep. 12, 2019

Related U.S. Application Data

(60) Provisional application No. 62/640,421, filed on Mar. 8, 2018.

(51) Int. Cl.
| *A61J 1/14* | (2006.01) |
| *A61L 2/26* | (2006.01) |
| *A61L 2/07* | (2006.01) |
| *A61L 2/18* | (2006.01) |
| *A61L 2/20* | (2006.01) |
| *A61M 5/142* | (2006.01) |
| *A61M 5/145* | (2006.01) |

(52) U.S. Cl.
CPC .............. *A61J 1/1443* (2013.01); *A61L 2/07* (2013.01); *A61L 2/18* (2013.01); *A61L 2/20* (2013.01);
(Continued)

(58) Field of Classification Search
CPC .... A61J 1/443; A61L 2/07; A61L 2/18; A61L 2/20; A61L 2/26; A61L 2202/18;
(Continued)

(56) References Cited

U.S. PATENT DOCUMENTS

| 9,456,956 B1 | 10/2016 | Webster et al. |
| 2006/0095014 A1* | 5/2006 | Ethelfeld .............. A61M 5/158 604/506 |

(Continued)

FOREIGN PATENT DOCUMENTS

| EP | 1495775 A1 * | 1/2005 | ........ A61M 5/14248 |
| WO | 02094352 A2 | 11/2002 | |

(Continued)

OTHER PUBLICATIONS

International Search Report and Written Opinion dated Nov. 4, 2019 in corresponding International Patent Application No. PCT/IB2019/051910.

*Primary Examiner* — Timothy P. Kelly
*Assistant Examiner* — Stephanie A Shrieves
(74) *Attorney, Agent, or Firm* — Volpe Koenig (57) ABSTRACT

A device and method is disclosed for assembling a container holder in a clean environment, aseptically adding a solution to a primary container, inserting the primary container into the container holder, applying a first barrier to the container holder, sterilizing the container holder comprising the primary container and the applied first barrier to provide a sterilized container holder, assembling a fluid path module in a clean environment, the assembling comprising applying a second barrier to a first end of the sterilized fluid path module, sterilizing the fluid path module to provide a sterilized fluid path module and assembling a delivery device comprising the sterilized container holder and the sterilized fluid path module.

9 Claims, 7 Drawing Sheets

(52) U.S. Cl.
    CPC ............ *A61L 2/26* (2013.01); *A61L 2202/18* (2013.01); *A61L 2202/23* (2013.01); *A61L 2202/24* (2013.01); *A61M 2005/14252* (2013.01); *A61M 2005/14573* (2013.01)

(58) Field of Classification Search
    CPC ............ A61L 2202/24; A61L 2202/23; A61M 2005/14252; A61M 2005/14573; A61M 5/14248; B65B 1/20; B65B 1/22; B65B 1/24; B65B 1/26
    USPC .......................................................... 141/11
    See application file for complete search history.

(56) References Cited

U.S. PATENT DOCUMENTS

| | | | |
|---|---|---|---|
| 2008/0009805 A1* | 1/2008 | Ethelfeld | A61M 5/14248 604/180 |
| 2009/0076453 A1* | 3/2009 | Mejlhede | A61M 5/158 604/151 |
| 2011/0009825 A1* | 1/2011 | Chong | F04B 23/02 604/152 |
| 2015/0057613 A1* | 2/2015 | Clemente | A61M 5/14248 604/148 |
| 2015/0359965 A1* | 12/2015 | O'Connor | A61M 5/16822 604/123 |
| 2016/0008536 A1* | 1/2016 | Gravesen | A61M 5/14248 604/151 |
| 2019/0022306 A1* | 1/2019 | Gibson | A61M 5/14566 |
| 2019/0374707 A1* | 12/2019 | Damestani | A61M 5/24 |

FOREIGN PATENT DOCUMENTS

| | | |
|---|---|---|
| WO | 2011014514 A1 | 2/2011 |
| WO | 2012088277 A2 | 6/2012 |

* cited by examiner

STERILIZATION FLUID PATH WITH BARRIER REMOVAL

This application claims the benefit of U.S. Provisional Application No. 62/640,421 having a filing date of Mar. 8, 2018, which is incorporated by reference as if fully set forth.

BACKGROUND

In medical devices such as combination patch pumps, which include a pump and a solution (e.g., drug), the solution, while inside the pump, cannot pass a sterilization process for a fluid path that transports the solution. Using an unsterilized fluid path can cause adverse effects such as infections and is unacceptable from a risk management perspective.

SUMMARY

A device and method is disclosed for assembling a container holder in a clean environment, aseptically adding a solution to a primary container, inserting the primary container into the container holder, applying a first barrier to the container holder, sterilizing the container holder comprising the primary container and the applied first barrier to provide a sterilized container holder, assembling a fluid path module in a clean environment, the assembling comprising applying a second barrier to a first end of the sterilized fluid path module, sterilizing the fluid path module to provide a sterilized fluid path module and assembling a delivery device comprising the sterilized container holder and the sterilized fluid path module.

BRIEF DESCRIPTION OF THE DRAWINGS

A more detailed understanding may be had from the following description, given by way of example in conjunction with the accompanying drawings wherein.

DETAILED DESCRIPTION

Examples of sterilized delivery device implementations will be described more fully hereinafter with reference to the accompanying drawings. These examples are not mutually exclusive, and features found in one example can be combined with features found in one or more other examples to achieve additional implementations. Accordingly, it will be understood that the examples shown in the accompanying drawings are provided for illustrative purposes only and they are not intended to limit the disclosure in any way. Like numbers refer to like elements throughout.

Below are described an apparatus and methods for delivering solutions such as pharmaceutical drugs and/or biologics to a patient. The apparatus and methods may allow for prescription or standard off-the-shelf drug cartridges, vials, syringes, or other containers (hereinafter generally referred to as a container), to be utilized without compromising the sterility of the solution. This may enable a patient to self-administer a solution in a self-contained wearable patch pump form factor that is cost effective and comfortable to wear. The disclosure subject matter provided herein may allow the manufacturing and use of a drug delivery device that includes a sterilized fluid path and container holder.

Figure 1A:
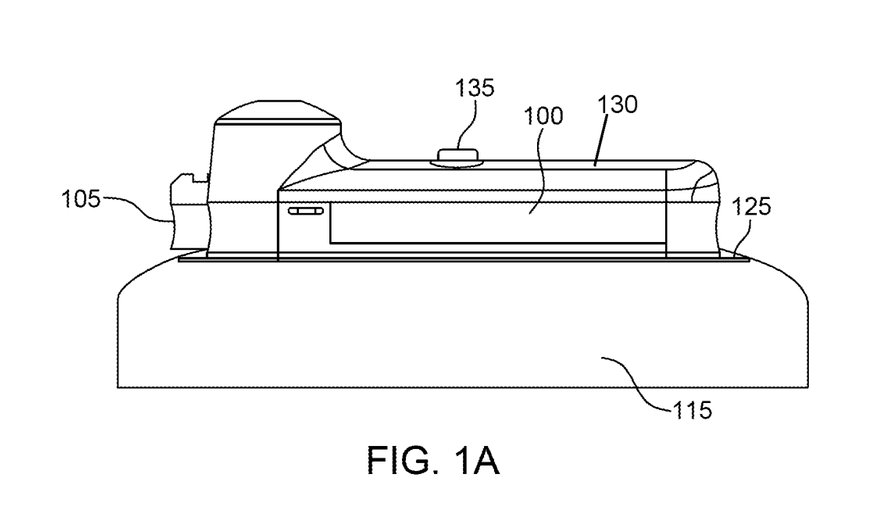
FIG. 1A is a graphic depiction of a patch pump for a user.
Figure 1B:
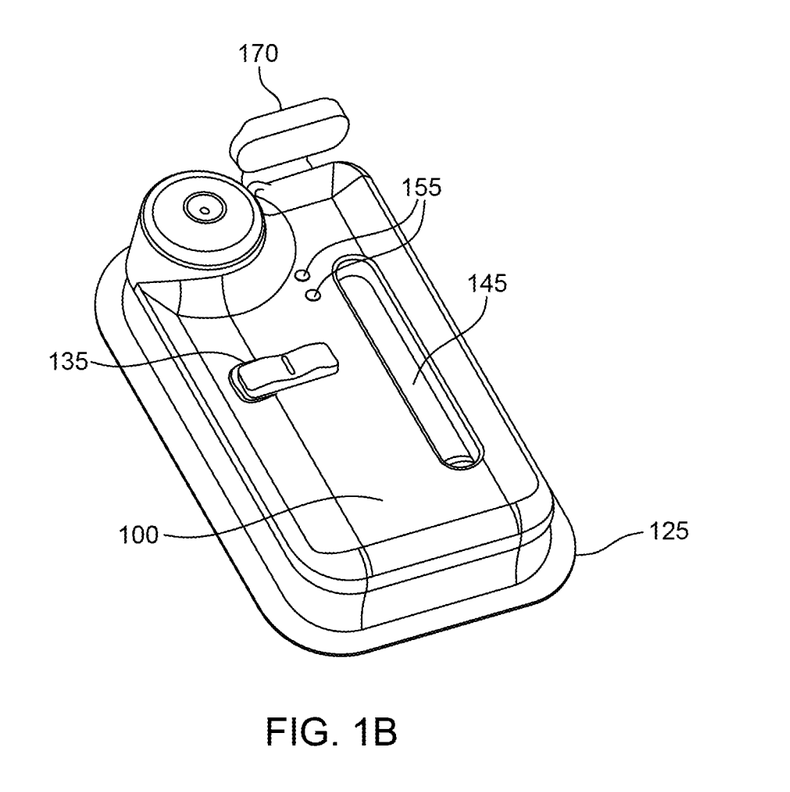
FIG. 1B is a graphic depiction of the outer casing of an example of a patch pump.
Figure 1C:
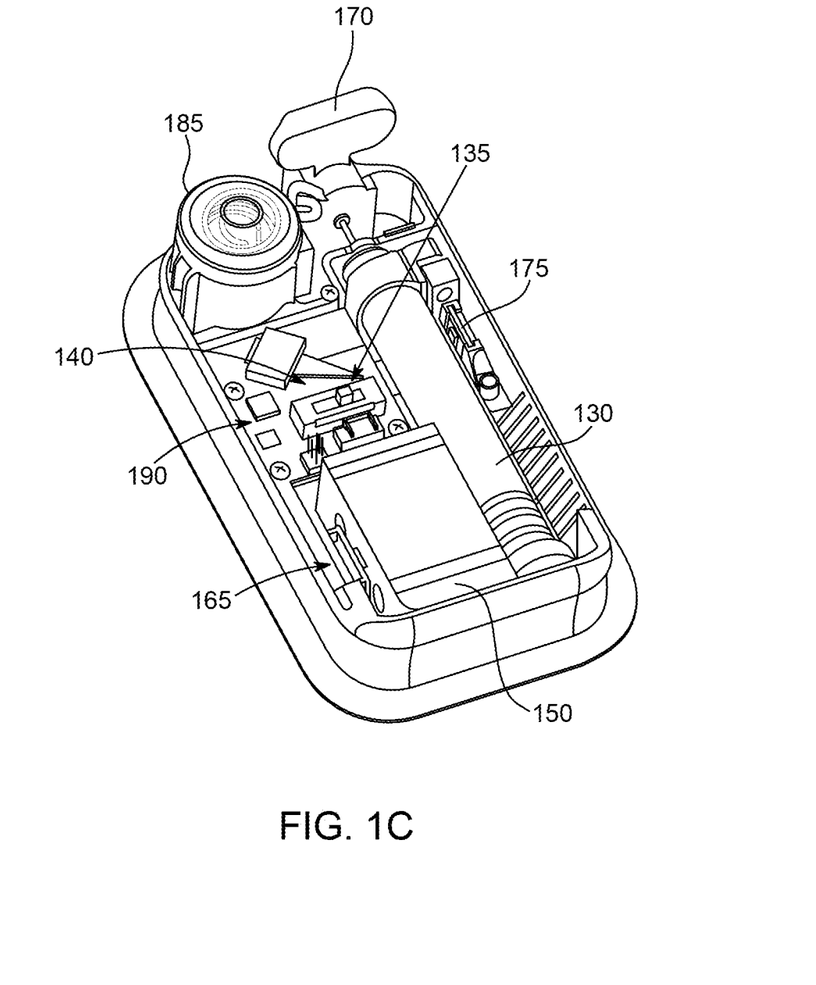
FIG. 1O is a graphic depiction of an example of a patch pump with the outer casing removed.

FIGS. 1A-1C show an example delivery device is shown via patch pump 100, which may be used with the sterilized container holder and sterilized fluid path as further described herein. A sterilized container holder may be provided in accordance with the subject matter disclosed herein. A delivery device may include such a sterilized container holder, which may connect to a sterilized container holder, in accordance with the subject matter disclosed herein. It will be understood, however, that patch pump 100 is an example, and other patch pumps or delivery devices may be used to implement a sterilized fluid path and sterilized container holder, as disclosed herein.

FIG. 1A is a graphic depiction of a patch pump 100 on a patient 115. The patch pump 100 includes a base 125 that contacts the patient's skin. In some embodiments, the base 125 includes an adhesive liner that affixes the patch pump 100 to the patient 115. The patch pump 100 may further include a user flow control switch 135. The user flow control switch 135 may enable a user to pause and control the flow rate of a solution. The patch pump 100 further includes a start button 105 that may be pressed by a user to cause a cannula and/or needle to be inserted into the patient and the solution to flow from a drug container 130 through the cannula and/or needle into the patient.

As shown in FIG. 1B, the patch pump 100 may further include a drug viewing window 145. This viewing window may enable a user to view the amount of a solution that remains in the drug container 130. The patch pump 100 may also include one or more visual indicators 155. The visual indicators 155 provide feedback on the operational status of the system. The operational status of the system may include warnings such as an over/under temperature warning, drug expiration warning and over/under pressure warning. In addition, the operational status may include information indicating that the drug is being administered, how much time is remaining for the drug dosage to be completed and the current flow rate. The visual indicators may include LEDS, LCD displays or other similar display technologies known in the art. The information that is displayed by visual indicators may also be wirelessly transmitted to a mobile computing device such as a smart phone utilizing any of the wireless communication methods known in the art.

The patch pump 100 may further include a removable safety 170. The removable safety mechanically engages the start button 105 and prohibits the start button 105 from being involuntary pressed.

FIG. 1C shows additional components of a patch pump 100. The patch pump 100 may also include a needle insertion component 185 that is mechanically connected to the start button 105. In addition, the patch pump 100 includes an electronic circuit board 140 that includes control circuitry for the visual indicators 155, user flow control switch 135 and a pressurization system 150. In addition, the electronic circuit board 140 may be communicatively connected to one or more sensors. These sensors may include pressure sensor 165 and proximity sensor 175 or any other applicable sensor such as a haptic feedback sensor (not shown) or other indicator. The electronic circuit board 140 may also include a memory 190. The memory 190 may store dosing instructions for the administration of the solution. In addition, the memory 190 may also store information regarding the administration of the solution. This information IT may include, time, date, and flow rate when the solution was administered. The electronic circuit board 140 may control the visual indicators 155 and the pressurization system 150 based on the information stored in the memory and the feedback from the sensors. The electronic circuit board 140 may include a communication module that enables the transmission of information stored in the memory 190 to a wireless computing device. In addition, the communication module may also receive updated dosing instructions that are subsequently stored in the memory 190.

According to the implementations disclosed herein, a delivery device may be assembled such that a sterilized container holder and a sterilized fluid path are provided to operate the delivery device. The sterilized container holder and the sterilized fluid path may be assembled via two separate processes such that they may be provided as separately packaged components. By providing the sterilized container holder and the sterilized fluid path as separately packaged components, a user may be able to use combinations two or more different container holders (e.g., two or more different drugs) with different sterilized fluid path components. For example, a first sterilized container holder and a first sterilized fluid path may be used in conjunction with a patch pump at a first time. Subsequently, a second sterilized container holder with a different drug than the first sterilized container holder and a second sterilized fluid path that is similar to the first sterilized fluid path may be provided. For example, multiple sterilized fluid path components may be bought as a pack of two or more sterilized fluid path components such that they can be used with different drugs via different sterilized container holders.

As disclosed herein, a septic process may be used when transferring or handling a solution (e.g., a drug) and a sterilization process may apply to components where the transfer or contamination of a solution is not applicable.

A sterilized container holder may be assembled such that a non-sterilized container holder may be provided in a clean environment. A clean environment may be, for example, an ISO certified clean room. The container holder may go through a sterilization process either inside or outside the clean environment. A solution, such as a drug, may be inserted into a primary container, inside a septic environment. The primary container may be a sterilized primary container. The solution may be inserted into the primary container via an aseptic filling technique. The aseptically filled primary container containing the solution may then be stoppered to seal the solution inside of the primary container, resulting in an overall aseptic insertion of the solution into the primary container. The stoppered primary container with the aseptically filled solution may be inserted into the container holder after the container holder is sterilized, resulting in a sterilized container holder with a primary container including a solution. The sterilized container holder may include a barrier, as further disclosed herein, that seals the sterilized container holder such that the sterilized container holder maintains its sterilization.

A sterilized fluid path may be assembled in a clean room. The fluid path may include a penetration needle, a channel via which the solution traverses, and a user needle configured to insert into a user or into a cannula to provide the solution to a user. The penetration needle may, as further disclosed herein, receive and/or draw solution from a primary container. The channel may be a line, pipe, hose, or other mode to transport fluid from at least the penetration needle to the user needle. The user needle may be configured to insert into a user or to provide fluid to a cannula or other needle that provides the solution to a user. As used herein, the sterilized fluid path and/or fluid path may also include a drive module. The drive module may be configured to cause the solution to be driven from the primary container, through the sterilized fluid path, and to a user. The sterilized fluid pathway may include one or two barriers, as further disclosed herein, that seal the sterilized fluid path such that the sterilized fluid path maintains its sterilization. A first such barrier may be on the end where the penetration needle is located and a second such barrier may be on the end where the user needle is located.

As described herein, a clean environment may be a clean room or other environment that meets a given standard. Clean rooms may be classified according to the cleanliness level of the air inside them. The clean room class may correspond to the level of cleanliness the room complies with, according to the quantity and size of particles per volume of air. The primary authority in the US and Canada is the ISO classification system ISO 14644-1, though it will be understood that the clean environment disclosed herein is not limited to the ISO classification. This standard includes the cleanroom classes ISO 1, ISO 2, ISO 3, ISO 4, ISO 5, ISO 6, ISO 7, ISO 8 and ISO 9, with ISO 1 being the "cleanest" and ISO 9 the "dirtiest" class (but still cleaner than a regular room). The most common classes are ISO 7 and ISO 8.

Figure 2A:
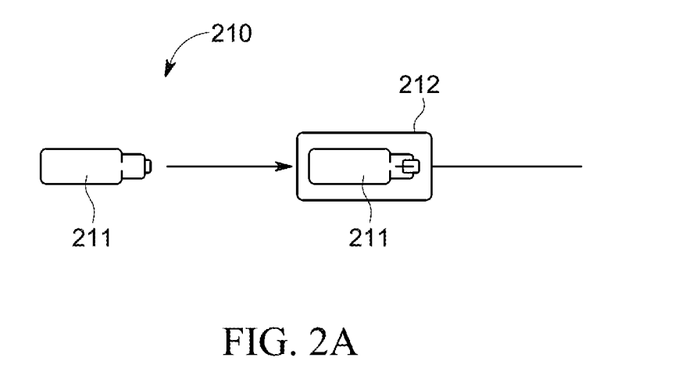
FIG. 2A is a graphical depiction of a container holder.

FIG. 2A shows an empty container holder 211 sterilization process 210. The empty container holder 211 may be assembled, manufactured, prepared or otherwise provided in a clean environment such as an ISO certified clean room (e.g., ISO 8), as disclosed herein. During the sterilization process 210, the container holder may be handled or otherwise manipulated by a robotic arm or other machine, or may be handled or otherwise manipulated by a user. As shown, the empty container holder 211 may experience sterilization at 212 such that the container holder may be sterilized to remove particles, dust, bacteria, contaminants, or other components that are not desirable.

Figure 2B:
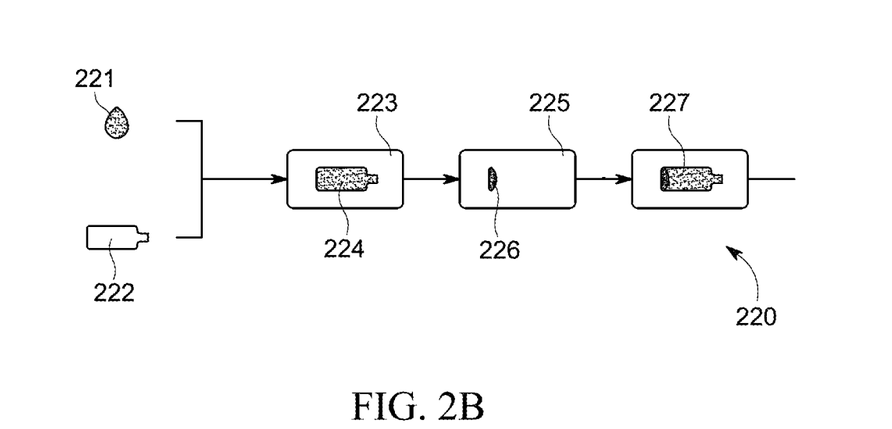
FIG. 2B is a graphical depiction of primary container with solution, inserted into a container holder.

FIG. 2B shows a clean assembly 220 during which solution 221 is aseptically inserted and stored in a primary container 222, stoppered, and inserted into a sterilized container holder 227. The container holder 227 may be assembled, manufactured, prepared or otherwise provided in a clean environment such as an ISO certified clean room (e.g., ISO 5), as disclosed herein. As shown, a solution 221 may be inserted into primary container 222 via an aseptic filling 223. Aseptic filling 223 may also include sterilization of the solution 221, sterilization of the primary container 222, and conservation of sterility during the filling. Equipment and packaging materials used during the aseptic filing 223 may be sterilized with various medium or combination of mediums such as via saturated steam, superheated steam, hydrogen peroxide, heat, and/or other treatments.

As shown in FIG. 2B, a stopper 226 may be applied to an aseptically filled primary container 224 at the stoppering step 225. The stoppering step 225 may include applying the stopper 226 to the aseptically filled primary container 224 via any applicable technique such as forced or mechanical stoppering such that the stopper 226 seals the solution 221 inside the aseptically filled primary container 224.

The sterilized container 211 of FIG. 2A may be provided such that the stoppered aseptically filled primary container 224 is inserted into the empty container holder 211 to provide a sterilized container holder 227. The aseptically filled primary container 224 may be inserted into the empty container holder 211 in a clean environment, which may be the same as or different from the clean environment in which the solution 221 is aseptically filled into the primary container 222. As further disclosed herein, a barrier may be applied to the sterilized container holder 227.

Figure 2C:
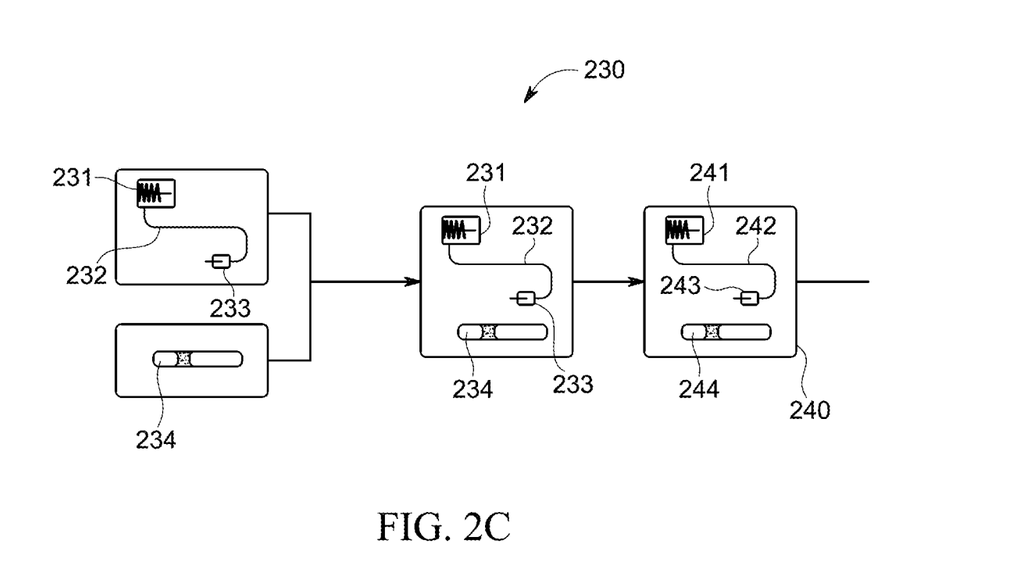
FIG. 2C is a graphical depiction of a sterilized fluid path module.

FIG. 2C shows a penetration needle 231, a channel 232, and a user needle 233 such that the channel 232 connects the penetration needle 231 to the user needle 233. As disclosed herein, the penetration needle 231 is configured to puncture a primary container (e.g., aseptically filled primary container 224 of FIG. 2B) inside a container holder (e.g., the sterilized container holder 227 of FIG. 2B) such that solution (e.g., solution 221 of FIG. 2B) is provided to the channel 232 and to a user via the user needle 233.

The fluid path module 230 may include drive module 234, penetration needle 231, channel 232, and user needle 233 that are assembled, manufactured, prepared or otherwise provided in a clean environment such as an ISO certified clean room (e.g., ISO 7), as disclosed herein. The drive module 234 may include components that cause a solution to be inserted into and/or traverse through the fluid path module 230 and, specifically, via the penetration needle 231, channel 232, and user needle 233. The device module may include on or more electronic components, mechanical components, or a combination of the same. According to an implementation, a drive module 234 may not be provided such that a patch pump, patch pump component(s), or other component may substitute for the functionality provided by the drive module 234.

The fluid path module 230 may experience sterilization, to provide a serialized fluid path module 240, such that the components of the fluid path module 230 including the penetration needle 231, channel 232, user needle 233 and drive module 234 are sterilized to remove particles, dust, bacteria, contaminants, or other components that are not desirable. As shown, the sterilized fluid path module 240 may include a sterilized penetration 241, a sterilized channel 242, sterilized user needle 243 and sterilized drive module 244. The sterilized fluid path module 240 may be sealed or otherwise treated to mitigate contamination.

Figure 2D:
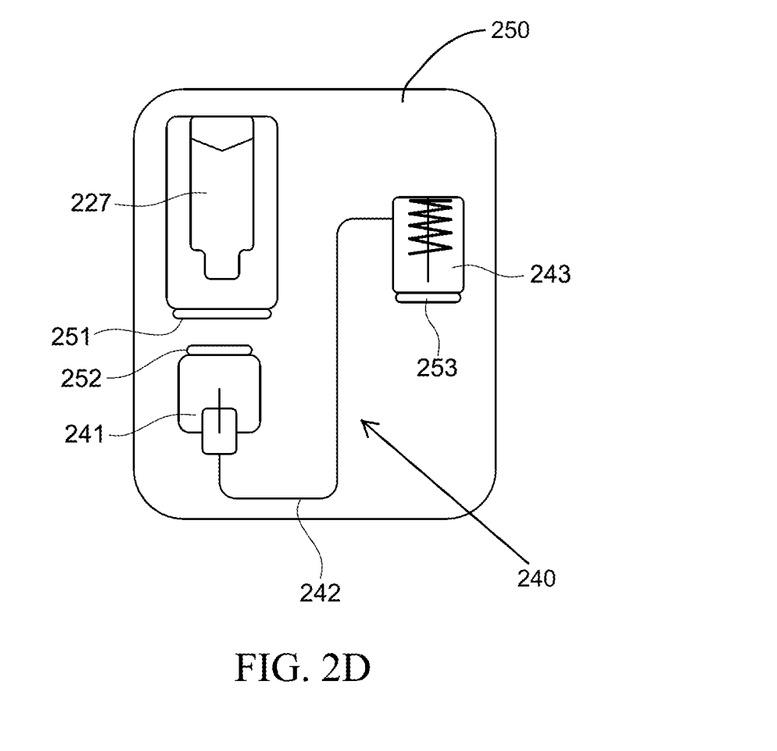
FIG. 2D is a graphical depiction of barriers associated with a sterilized container holder and fluid path.

As shown in FIG. 2D, a delivery device 250 may be assembled and may include the sterilized container holder 227 and a sterilized fluid path 240 including sterilized penetration 241, a sterilized channel 242, and sterilized user needle 243. The delivery device 250 may be a standalone device or may be configured to incorporate the sterilized container holder 227 and sterilized fluid path 240 into its operation. For example, the delivery device 250 may be patch pump 100 of FIG. 1A-FIG. 10, a different patch pump or a different device configured to provide a solution.

As shown in FIG. 2D, one or more barriers may be applied to the sterilized container holder 227 and/or sterilized fluid path 240. A container holder barrier 251 may be applied to the container holder 227. A penetration needle barrier 252 may be applied to a first end of the sterilized fluid path 240 (e.g., on the end closest to the sterilized penetration needle 241). A user needle barrier 253 may be applied to a second end of the sterilized fluid path 240. The barriers 251, 252, and 253 may all be the same or may be similar or, alternatively, may be different from each other. The material for barriers 251, 252, and 253 may be any applicable single layer or multi layer material configured to provide a seal or barrier between the component that the respective barrier 251, 252 or 253 is attached to and anything external to the component. As non-limiting examples, the material for barriers 251, 252, and 253 may be aluminum foil, Tyvek or material with properties the same as or similar to Tyvek (collectively referred to as "Tyvek" herein), or a thermoplastic elastomer (TPE).

Figure 3:
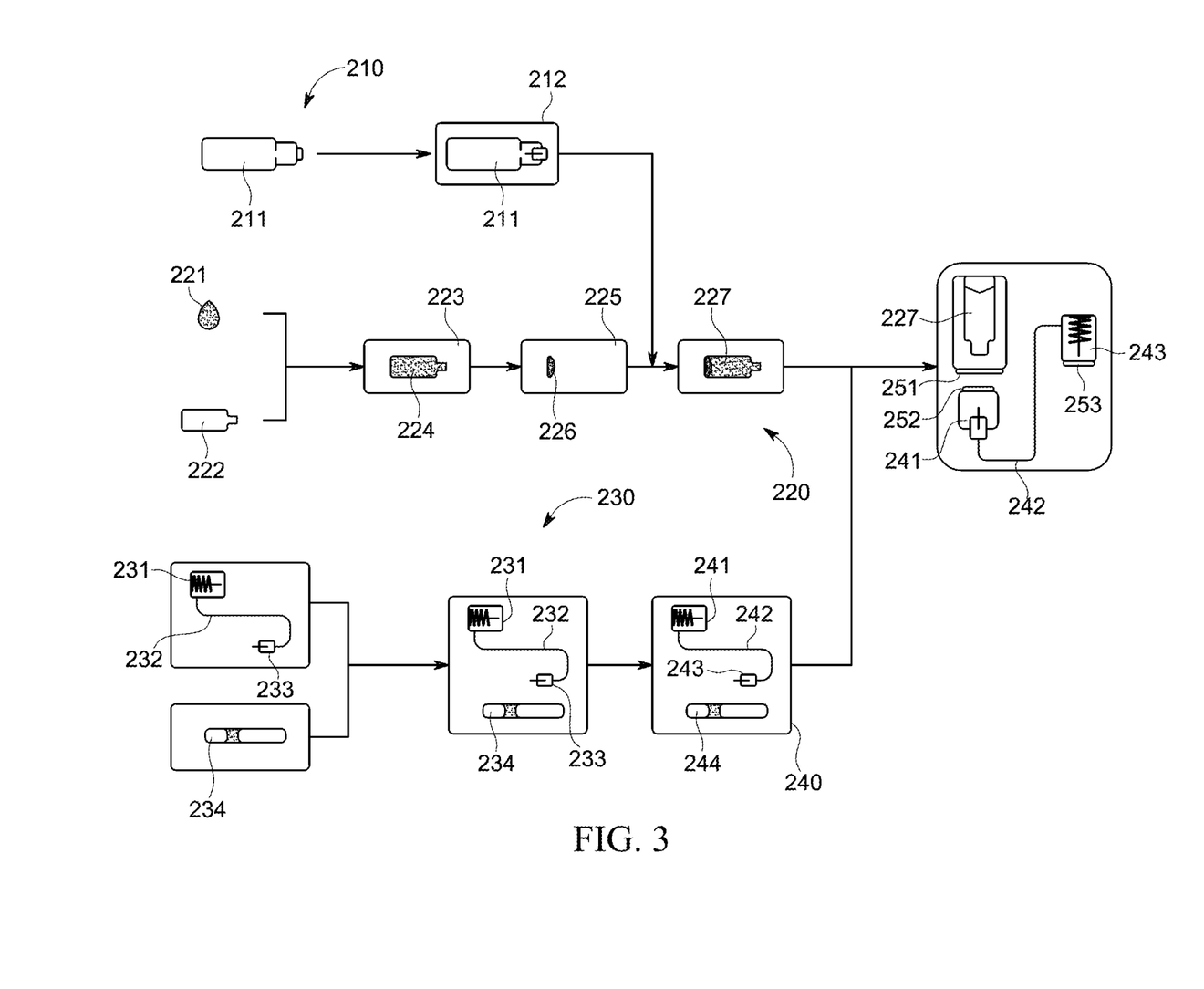
FIG. 3 is a graphical depiction of a sterilization process.

FIG. 3 shows a complete diagram including the components and steps provided in FIG. 2A-D. As shown, at 210, an empty primary container 211 is provided in a clean environment and is sterilized at 212. A solution 221 is aseptically inserted, at 223, into a primary container 222. The primary container 222 is filled with the solution 221 and is stoppered 225 via stopper 226. The stoppered and aseptically filed primary container 224 is placed inside the container holder (after sterilization 212) such that a sterilized container holder 227 includes a primary container 224 including the solution 221.

A penetration needle 231, channel 232, and user needle 233 is assembled with a drive module 234 and sterilized in a clean environment to result in a sterilized fluid path 240 that includes a sterilized penetration needle 241, sterilized channel 242, sterilized user needle 243 and sterilized drive module 244.

A delivery device 250 includes the sterilized container holder 227 and sterilized fluid path 240 as well as container holder barrier 251 attached to the sterilized container holder 227, penetration needle barrier 252 attached to a first end of the sterilized fluid path 240 near the sterilized penetration needle 241, and a user needle barrier 253 attached to a second end of the sterilized fluid path 240 near the sterilized user needle 243.

The barrier(s) (i.e., container holder barrier 251, penetration needle barrier 252, and/or user needle barrier 253) may be configured to seal the components that they are attached to and may further be configured to maintain the sterility of a component that they are attached to. For example, the container holder barrier 251 may be configured to seal the sterilized container holder 227 such that the sterility of the sterilized container holder 227 is maintained as a result of seal provided by the container holder barrier 251.

It should be noted that the sterilized container holder 227 and the sterilized fluid path 240 may be manufactured and/or shipped at the same time or may be manufactured/and or shipped as separately packaged items. Such flexibility may reduce cost and allow separate uses of the sterilized container holder 227 and the sterilized fluid path 240.

Figure 4A:
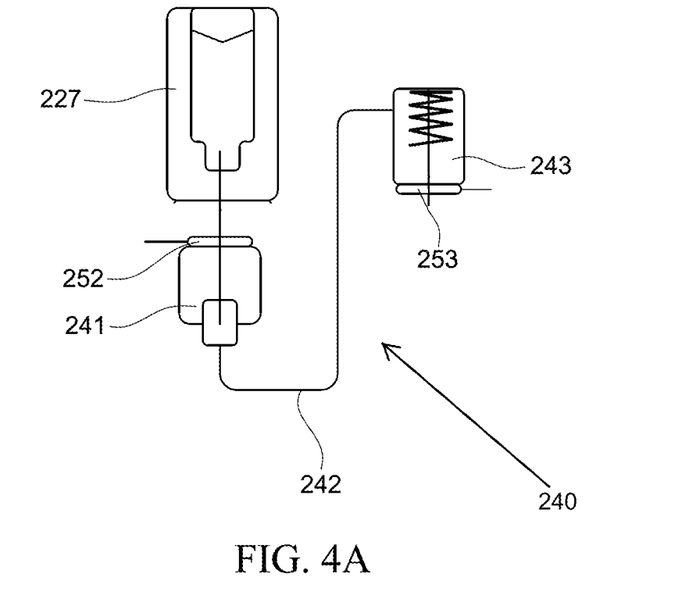
FIG. 4A is a graphical depiction of a penetration needle and a user needle penetrating barriers.

FIG. 4A shows an implementation of the disclosed subject matter where the penetration needle 241 is configured to penetrate a surface of the sterilized fluid path 240, penetration needle barrier 252, and a surface of the sterilized container holder 227 after the container holder barrier 251 is removed. As shown, the sterilized penetration needle 241 may be inserted through a surface of the fluid path 240 that is adjacent or proximal to the sterilized penetration needle 241 and through the container holder barrier 251, and into the sterilized container holder 227. Note that the container holder barrier 251 may be removed to avoid contamination associated with the outside of the container holder barrier 251. The penetration by the penetration needle 241 may be a result of an electronic or mechanical force applied to the sterilized penetration needle 241 (e.g., via which the sterilized penetration needle 241 is pushed or pulled towards the sterilized container holder 227) and/or an electronic or mechanical force applied to the sterilized container holder 227 (e.g., via which the sterilized container holder is pushed or pulled towards the penetration needle 241).

According to the implementation shown in FIG. 4A, the sterilized user needle 243 is configured to penetrate a surface of the sterilized fluid path 240 and sterilized user needle barrier 253. As shown, the sterilized user needle 243 may be inserted through a surface of the fluid path 240 that is distal from the sterilized penetration needle 241 and through the user needle barrier 253. The penetration by the sterilized user needle 243 may be a result of an electronic or mechanical force applied to the sterilized user needle 243 (e.g., via which the sterilized user needle 243 is pushed or pulled towards user needle barrier 253) and/or an electronic or mechanical force applied in the direction from the user needle barrier 253 towards sterilized user needle 243.

Figure 4B:
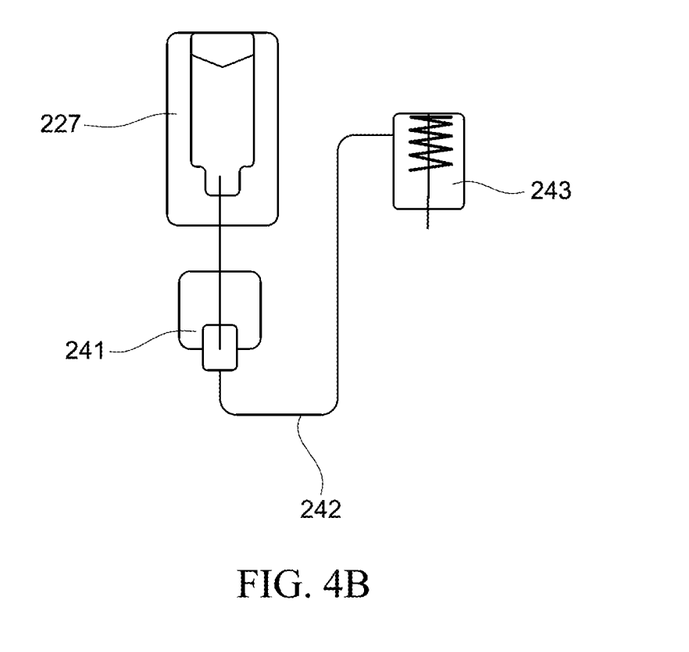
FIG. 4B is a graphical depiction of a penetration needle and a user needle penetrating surfaces.

FIG. 4B shows an implementation of the disclosed subject matter where the barrier(s) (i.e., container holder barrier 251, penetration needle barrier 252, and/or user needle barrier 253) are removed prior to penetration by the sterilized penetration needle 241 and/or sterilized user needle 243. The barrier(s) may be removed by, for example, a user or may be removed automatically based on an electrical or mechanical movement, which causes removal of the barrier(s). For example, a patch pump (e.g., such as patch pump 100 of FIG. 1A-FIG. 10) may include mechanisms to remove barriers such as the container holder barrier 251, penetration needle barrier 252, and/or user needle barrier 253. One or more barriers may be removed at the same time or each barrier of the multiple barriers may be removed at different times.

According to the implementation shown in FIG. 4B, the sterilized penetration needle 241 may penetrate one or more sterilized fluid path 240 surfaces, and one or more surfaces of the sterilized container holder 227 and may be configured to provide solution contained in the sterilized container holder 227 into the sterilized channel 242. The user needle may be configured to penetrate one or more sterilized fluid path 240 surfaces and may be configured to provide solution from the sterilized channel 242 to a user or other component(s) which then provide the solution to a user.

Figure 5:
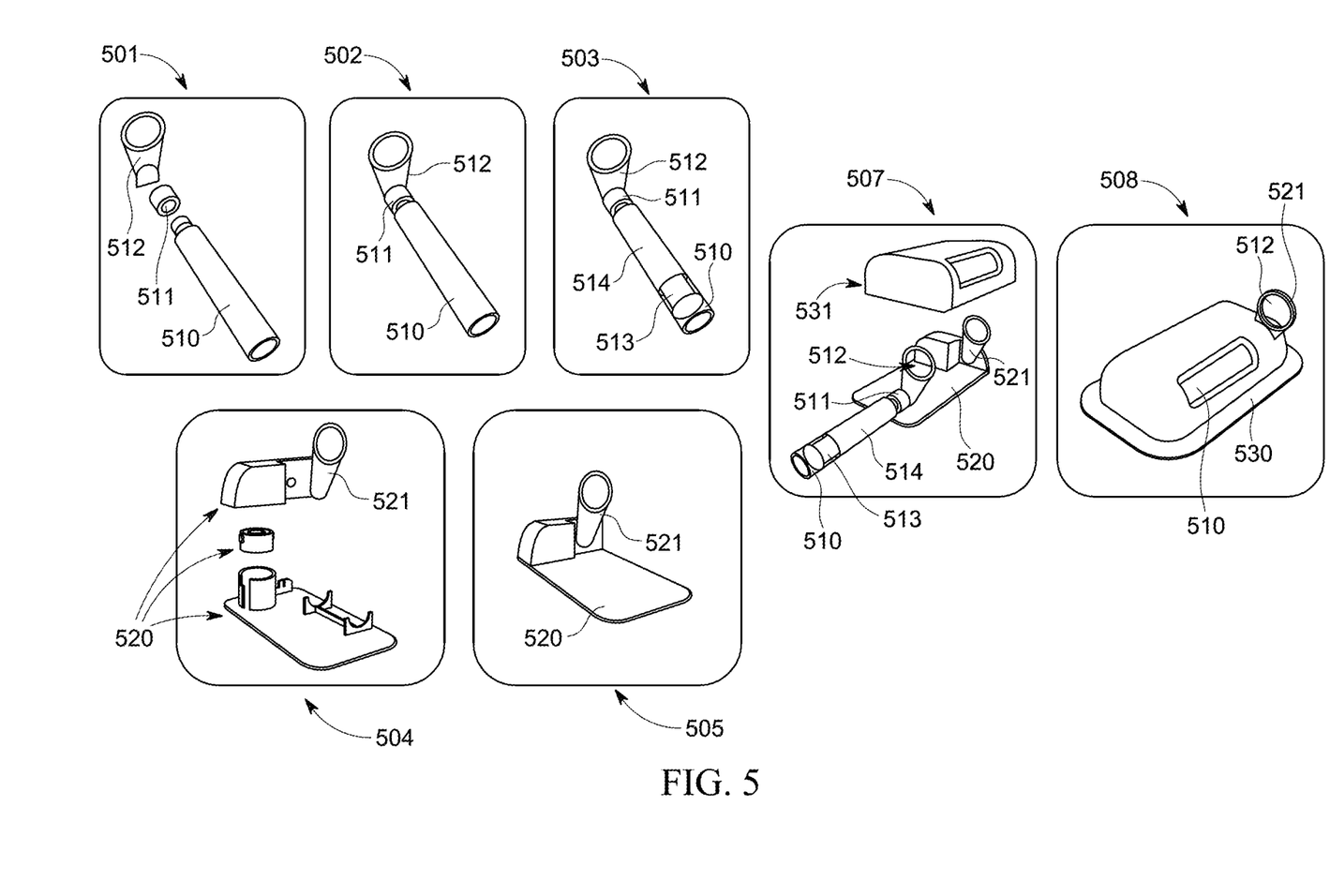
FIG. 5 is a graphical description of assembling a delivery device.

FIG. 5 shows a process with components in accordance with an implementation disclosed herein. As shown, a container holder may be assembled at 501 and may include primary container 510, container holder 511, and container holder barrier 512. At 502, the assembled container holder may be sterilized. The assembly 501 and/or sterilization may occur in a clean room, as disclosed herein. A solution 514 may be aseptically added to the primary container 510, at 503. The solution 514 may be sealed via a stopper 513 at 503.

As shown at 504 in FIG. 5, components of a fluid path 520 along with a penetration needle barrier 521 may be assembled. The fluid path 520 and penetration needle barrier 521 may be sterilized at 505. The assembly 504 and/or sterilization may occur in a clean room, as disclosed herein.

As noted herein, the sterilized primary container 510 and/or container holder 511 assembled at step 503 may be manufactured and shipped at the same location and time or at a different location and time than the sterilized fluid path assembled at 505.

A delivery device 530 may be assembled at 507 and 508 such that a device component 531, the sterilized primary container 510, container holder 511, container holder barrier 512, fluid path 520, and penetration needle barrier 521 may be assembled to provide a delivery device 530.

Although features and elements are described above in particular combinations, one of ordinary skill in the art will appreciate that each feature or element can be used alone or in any combination with the other features and elements.

What is claimed is:

1. A method comprising:
   assembling a container holder in a clean environment;
   sterilizing the container holder;
   aseptically adding a solution to a primary container;
   inserting the primary container into the container holder;
   applying a first barrier to the container holder;
   sterilizing the container holder comprising the primary container and the applied first barrier to provide a sterilized container holder;
   assembling a fluid path module in a clean environment, the fluid path module comprising a penetration needle, a user needle, and a channel having one end directly connected to the penetration needle and an opposite end directly connected to the user needle, the assembling comprising applying a second barrier to a first end of the sterilized fluid path module at a location in proximity to a distal end of the penetration needle, and applying a third barrier to a second end of the sterilized fluid path module at a location in proximity to a distal end of the user needle;
   sterilizing the fluid path module to provide a sterilized fluid path module; and
   assembling a delivery device comprising the sterilized container holder and the sterilized fluid path module.

2. The method of claim 1, further comprising:
   activating the delivery device by removing the first barrier.

3. The method of claim 2, wherein activating the delivery device further comprises connecting the sterilized fluid path module to the sterilized container holder.

4. The method of claim 1, wherein connecting the sterilized fluid path module to the sterilized container holder comprises penetrating a container holder surface by the penetration needle.

5. The method of claim 1, wherein assembling the delivery device further comprises penetrating the second barrier by the penetration needle.

6. The method of claim 5, wherein assembling the delivery device further comprises removing the first barrier and penetrating a container holder surface by the penetration needle.

7. The method of claim 1, wherein activating the delivery device further comprises removing the third barrier and puncturing the second end of the sterilized fluid path module by a user needle.

8. The method of claim 1, wherein at least one of the first barrier and the second barrier is a septum material.

9. The method of claim 8, wherein the septum material is at least one of an aluminum foil, Tyvek, and a thermoplastic elastomer (TPE).

* * * * *